US008966662B2

(12) United States Patent
Belliappa

(10) Patent No.: US 8,966,662 B2
(45) Date of Patent: Mar. 3, 2015

(54) APPARATUS FOR A SLEEP MASK

(71) Applicant: Ajit Belliappa, New York, NY (US)

(72) Inventor: Ajit Belliappa, New York, NY (US)

( * ) Notice: Subject to any disclaimer, the term of this patent is extended or adjusted under 35 U.S.C. 154(b) by 0 days.

(21) Appl. No.: 13/730,731

(22) Filed: Dec. 28, 2012

(65) Prior Publication Data
US 2014/0182039 A1     Jul. 3, 2014

(51) Int. Cl.
*A61F 9/00*     (2006.01)
*A61F 9/04*     (2006.01)

(52) U.S. Cl.
CPC ...................................... *A61F 9/045* (2013.01)
USPC .............................................................. 2/15

(58) Field of Classification Search
USPC .......... 2/9, 15, 174; 128/206.23, 858; 602/54, 602/56, 74
See application file for complete search history.

(56) References Cited

U.S. PATENT DOCUMENTS

| | | | | |
|---|---|---|---|---|
| 2,874,385 | A * | 2/1959 | Wade | 2/15 |
| 3,068,863 | A * | 12/1962 | Bowman | 128/858 |
| 3,092,103 | A * | 6/1963 | Mower | 128/858 |
| 4,331,136 | A * | 5/1982 | Russell et al. | 128/858 |
| 4,635,625 | A * | 1/1987 | Teeple | 128/858 |
| 4,727,869 | A * | 3/1988 | Leonardi | 602/74 |
| 4,951,658 | A * | 8/1990 | Morgan et al. | 602/74 |
| 5,613,502 | A * | 3/1997 | Lee | 128/857 |
| 5,879,292 | A * | 3/1999 | Sternberg et al. | 600/300 |
| 5,918,600 | A * | 7/1999 | Durette | 128/857 |
| 7,036,928 | B2 * | 5/2006 | Schwebel | 351/62 |
| 8,458,812 | B2 * | 6/2013 | Kayerod | 2/9 |
| 2012/0192330 | A1 | 8/2012 | McMullen | |

FOREIGN PATENT DOCUMENTS

RU          41984 U1      11/2004

OTHER PUBLICATIONS

Authorized Officer T. Vladimirova, "Notification of Transmittal of the International Search Report and the Written Opinion of the International Searching Authority, or the Declaration"; Authorized Officer L. Karimova, "International Search Report" mailed Feb. 20, 2014; Authorized Officer L Karimova, "Written Opinion of the International Searching Authority" mailed Feb. 20, 2014. PCT/US2013/064460. 7 pages.
Authorized Officer: L. Karimova. "International Search Report PCT/US 2013/064460" Date of Completion of International Search: Nov. 25, 2013. 1 Page.

* cited by examiner

*Primary Examiner* — Tejash Patel
(74) *Attorney, Agent, or Firm* — Stetina, Brunda, Garred & Brucker

(57) ABSTRACT

An apparatus comprises a gauze layer comprising a gauze material, a first area, a gauze first side and a gauze second side. The gauze first side is configured to at least contact and cover a user's eyelid area where the gauze material mitigates irritation of the user's skin. A paper layer comprises a paper material, a paper first side and a paper second side. The paper first side comprises an adhesive area being configured to extend beyond the first area for removably joining to the user's skin. A tape layer comprises an opaque flexible material, a third area, a tape first side and a tape second side. The tape first side comprises an adhesive. The third area is at least as large as the first area. The gauze layer, the paper layer and the tape layer are combined to form a sleep mask.

20 Claims, 2 Drawing Sheets

APPARATUS FOR A SLEEP MASK

CROSS-REFERENCE TO RELATED APPLICATIONS

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to sleep masks. More particularly, the invention relates to a single use sleep mask.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. It is believed that some individuals may suffer from low quality of sleep and potential myriad related health problems due to exposure to light while sleeping or attempting to sleep. This problem may be mismanaged due to lack of understanding of how sensitive the human body's circadian rhythm, or sleep-wake cycle, can be to even minimal amounts of light.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, an aspect of the prior art generally useful to be aware of is that some devices are currently available for shielding a user's eyes from light such as, but not limited to, sleep masks. Prior art sleep masks are typically made of cloth or synthetic fiber and are generally intended for more than one use. Current sleep masks are often held in place with elastic bands or straps that wrap behind the head and attach with means such as, but not limited to, hook and loop material, snaps, buttons, etc. Often, the materials used in these currently available sleep masks do not completely block out all light and therefore may not replicate the effects of a completely dark environment, which may be needed for restful sleep. Also, skin and/or scalp irritation may be caused by single use or repeat use due to materials used in the mask or by the bands or straps that hold the mask on a user's head. Furthermore, an uncomfortable sensation of pressure on the face or head may result from the tension created by the elastic bands or straps behind the head. These bands or straps may also alter the contact point of the head with the sleeping surface, for example, without limitation, a pillow, mattress, or chair.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1A is an exploded view of the baseline strip, and FIG. 1B is a transparent top view of the baseline strip.

Figure 1A:
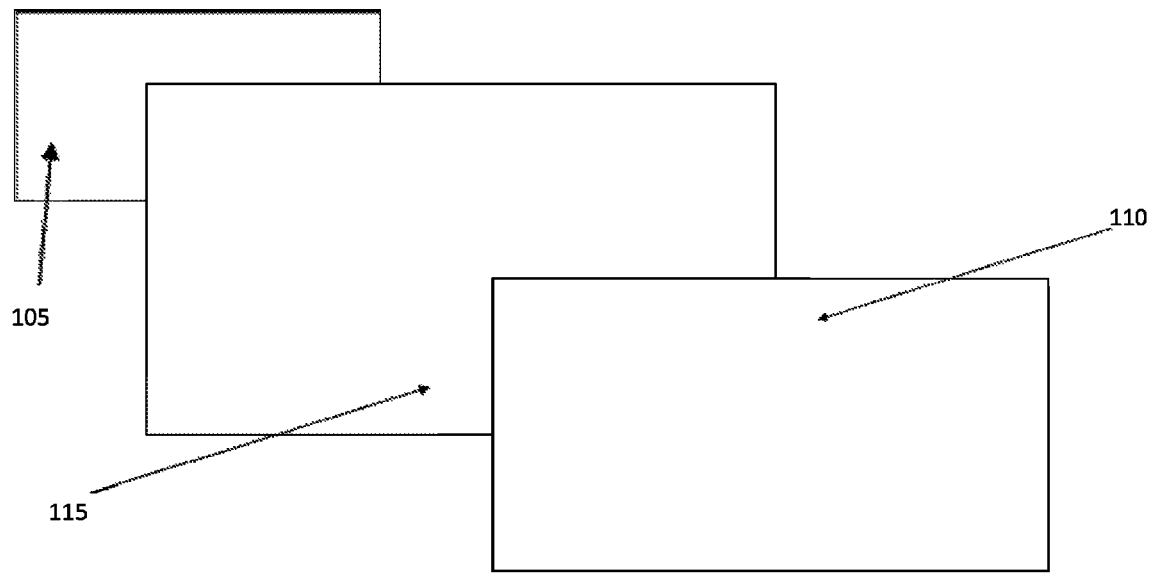
FIGS. 1A and 1B illustrate an exemplary baseline strip for a light blocking sleep mask system, in accordance with an embodiment of the present invention.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

An embodiment of the present invention provides a single use, opaque to light sleep mask that is held in place with tape. Some embodiments comprise a single mask to cover both eyes, and other embodiments comprise separate strips for each eye. Some embodiments may enable users to block out all natural and artificial light and achieve restful sleep no matter the time of day, without the use of medication or the need for modifications to their living space. Sleep masks according to some embodiments may be single use, lightweight, comfortable, opaque to light, adhesive strips that allow a user to replicate the benefits of a light free nighttime environment when artificial light is in use or during the daylight hours.

Figure 1B:
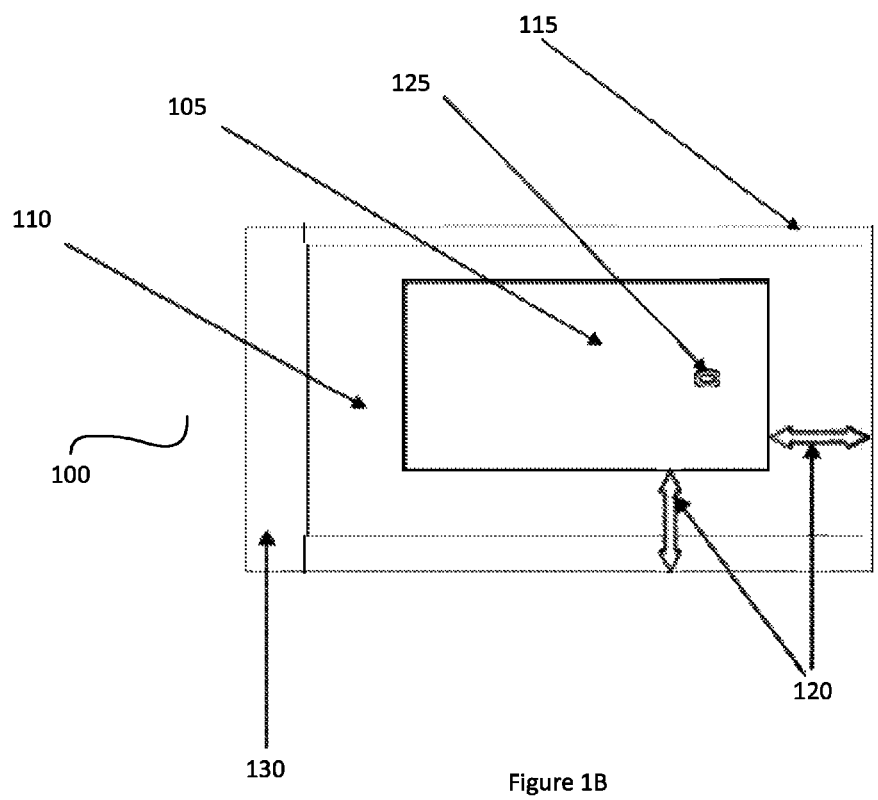

FIGS. 1A and 1B illustrate an exemplary baseline strip 100 for a light blocking sleep mask system, in accordance with an embodiment of the present invention. FIG. 1A is an exploded view of baseline strip 100, and FIG. 1B is a transparent top view of baseline strip 100. In the present embodiment, baseline strip 100 comprises a gauze layer 105, an electrical tape layer 110, and a paper tape layer 115. Non-adhesive gauze 105 is affixed to the adhesive side of adhesive paper tape 115. Paper tape 115 is only adhesive on one side. Electrical tape 110, which is also adhesive on only one side, is affixed by the adhesive side to the non-adhesive side of paper tape 115. Referring to FIG. 1B, this creates a layered strip with gauze 105 at the bottom, paper tape 115 in the middle, and electrical tape 110 on the top. Baseline strip 100 is compressed to generally eliminate any gaps between gauze 105, paper tape 115 and electrical tape 110. Gauze 105 is smaller in area than paper tape 115 to create an adhesive margin 120 around gauze 105. Margin 120 typically enables strip 100 to be adhered to a user's face. It is contemplated that the margin around the gauze in some embodiments may be larger or smaller depending on various factors such as, but not limited to, the overall size of the baseline strip, the size of the gauze area, the type of user for which the strip is intended, for example, without limitation, adults or children, etc. In the present embodiment, electrical tape 110 acts as a light blocking material. Those skilled in the art will readily recognize, in light of and in accordance with the teachings of the present invention, that a multiplicity of suitable materials may be used as the light blocking layer in some alternate embodiments such as, but not limited to, vinyl bundling tape, duct tape, thick fabrics, various plastics, etc.

In the present embodiment, referring to FIG. 1B, a tactile marker 125 is placed on the top, non-adhesive side of electrical tape 110. A multiplicity of suitable means may be used to create marker 125 such as, but not limited to, a stamped slight depression in electrical tape 110, a slightly raised ridge on electrical tape 110, a textured area, a raised button, tab, or nub adhered or otherwise attached to electrical tape 110, etc. Marker 125 indicates the central aspect of gauze 105 at the most medial or inner aspect of gauze 105. Again, referring to FIG. 1B, once assembled, baseline strip 100 may be placed on a non-adhesive plastic backing 130 that typically does not degrade the adhesive capability of paper tape 115. This generally allows for long-term storage of strip 110. Plastic backing 130 may be affixed to gauze 105 without leaving a sticky surface on gauze 105 after removal plastic backing 130. In some embodiments the plastic backing may only be affixed to paper tape 115 and not the rest of strip 100. A non-adhesive tab for strip 100 may be created by folding a portion of paper tape 115 back onto itself so that each side of this tab is non-adhesive. Alternative to or in addition to this non-adhesive tab, plastic backing 130 may be made longer than paper tape 115 to aid in removing strip 100 from backing 130.

In typical use of the present embodiment, a user requires two baseline strips 100 for each use, one strip 100 for each eye. The use of one strip 100 per may enable the eyes to be more effectively shielded from light as strips 100 may achieve a tighter seal around the eyes as opposed to a single strip model that covers both eyes. The use of one strip 100 per eye may also be more comfortable for the user. Strips 100 are typically applied one at a time, as the user may need to use both hands to apply each strip 100. In some instances, strips may be applied with one hand. If provided, the user grips the non-adhesive tab of strip 100 with the hand that matches the eye where the strip is being applied. For example, without limitation, if strip 100 is being applied to the left eye, the non-adhesive tab is gripped with the left hand. If no tab is provided, the user grips an outer edge of strip 100. One finger of the other hand may be placed over tactile marker 125. The user guides tactile marker 125 to the innermost or medial aspect of the eye with gauze 105 facing the eye. It is contemplated that some alternate embodiments may be implemented without a tactile marker. In typical use of these embodiments, the user may place the strip over the eye while taking care that the gauze is located over the eye. In the present embodiment, once strip 100 is in a satisfactory position, the user may affix paper tape 115 to the skin surrounding the eye, starting medially, then moving laterally, and then moving up and down. Once the user is satisfied that a light opaque seal has been achieved for the first eye by pressing down gently on paper tape 115, the above steps may be repeated for the other eye. When the user is ready to remove strips 100, strips 100 are typically removed one eye at a time. To remove strip 100, the non-adhesive tab or an edge of strip 100 is grasped, and then strip 100 is slowly peeled off moving from lateral to medial, outer to inner, reversing the direction of application. This slow removal may minimize trauma to skin and eyebrows. Once removed, strip 100 may be thrown away, and a fresh strip may be used the next time the user would like to shield his or her eyes from light. Those skilled in the art will readily recognize, in light of and in accordance with the teachings of the present invention, that a multiplicity of suitable methods may be used to apply and remove strips to and from a user's eyes. For example, without limitation, the user may affix paper tape 115 to the skin around the eye starting from the outer or lateral aspect of the eye and moving inward and may remove strips starting from the medial aspect moving outward.

The present embodiment may provide the complete blocking of light from the eyes and may help to maximize the possibility of restful sleep. Strip 100 may be used in almost any setting where the user is trying to sleep. Furthermore, strip 100 may be used at any time of day. If desired, the user may put sunglasses on over strips 100 if being used in a public place. It is beleieved that various different types of uers may be able to benefit from the use of these light blocking strips including, without limitation, individuals with insomnia, current users of medication for a sleep disorder, current users of the myriad number of purported sleep-inducing compounds such as, but not limited to, oral melatonin, city dwellers exposed to high levels of ambient light at night, night shift workers with difficulty adjusting their circadian rhythm, anyone exposed to artificial light in the hours before attempting to sleep, etc.

In typical use of the present embodiment, the only materials which contact the user's skin and eyes are typically paper tape 115 and gauze 105. The use of these materials and the lightweight nature of strip 100 may allow for regular and comfortable use of strip 100 over the course of the entire night even in users with sensitive skin. Also, using non-adhesive gauze 105 as the point of contact with the eye may reduce irritation to the eye as eyelid skin is thin and can be very sensitive and typically allows the eyelashes to remain unaffected when strip 100 is removed. Moreover, the single use design of strip 100 may minimize skin and scalp irritation caused by repeated use as oils from the skin and dead skin cells are not repeatedly brought back into contact with the user's skin. The use of adhesive paper tape 115 typically eliminates the need for elastic bands or straps which may minimize the uncomfortable sensation of pressure on the face and may help to eliminate the altered contact point created by currently available sleep masks. Strip 100 may also allow the user to sleep on his or her back or sides with equal comfort. If included, without limitation, the non-adhesive tab and tactile marker 125 help the user to easily apply and remove strip 100 without sticking to the user's fingers.

If desired, in some applications, baseline strips 100 may be used in conjunction with supplementary strips to provide a light free environment for the user. Supplementary strips are strips which are smaller than baseline strip 100. These supplementary strips may be equal in length to baseline strip 100 yet are narrower than baseline strip 100 or may be equal in width to baseline strip 100 yet shorter than baseline strip 100. Manufacture of the supplementary strips is similar to that of baseline strip 100 as described by way of example in the foregoing. These supplementary strips may enable the user to block out all light if the unique shape of his or her face does not allow baseline strip 100 to create a completely light opaque environment. Use of the supplementary strips involves the user placing one or more supplementary strips over any areas where light is visible at the margin of baseline strip 100 in especially light intense environments or in situations where the user has a facial shape that does not allow for creation of a light opaque seal based on use of baseline strip 100 alone.

It is contemplated that supplementary strips may be available in a multiplicity of suitable shapes including, without limitation, rectangles, rounded shapes, irregular shapes, etc. Furthermore, those skilled in the art will readily recognize, in light of and in accordance with the teachings of the present invention, that the baseline strips in some embodiments may be implemented in a multiplicity of suitable shapes. For example, without limitation, some embodiments may comprise strips with round, elliptical or irregular shapes to closely fit the shape of the orbital area. Other embodiments may be implemented as a one-piece mask rather than two baseline strips, as illustrated by way of example in FIG. 2.

Figure 2:
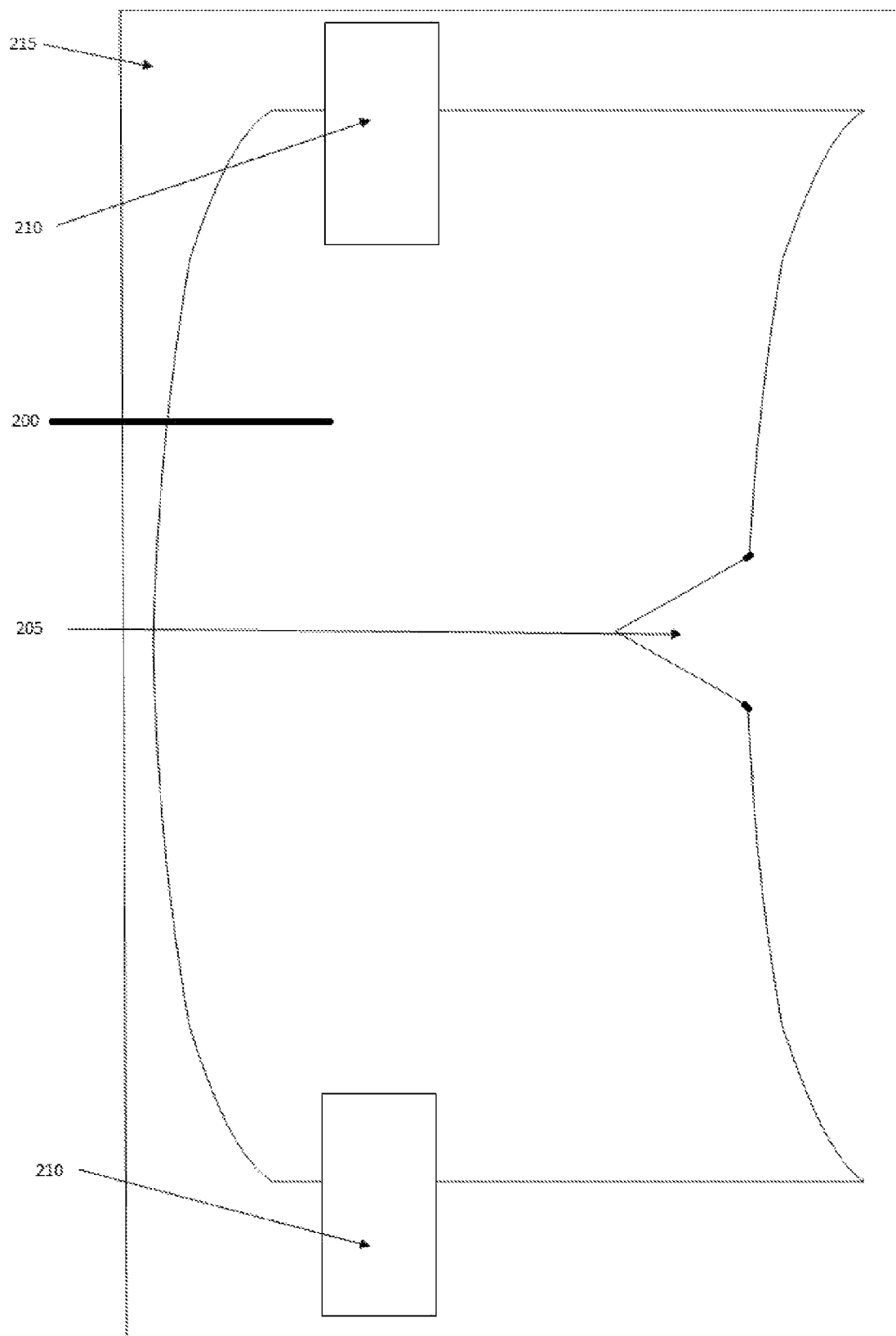
FIG. 2 is a diagrammatic top view of an exemplary one-piece, single use, disposable sleep mask, in accordance with an embodiment of the present invention.

FIG. 2 is a diagrammatic top view of an exemplary one-piece, single use, disposable sleep mask 200, in accordance with an embodiment of the present invention. In the present embodiment, sleep mask 200 is substantially opaque to light. Sleep mask 200 comprises a piece of double sided gauze that is cut to size and covered with electrical tape on one side. The electrical tape acts as a light blocking layer. It is contemplated that various different materials may be used as the light blocking layer in some alternate embodiments such as, but not limited to, duct tape, thick fabrics, various plastics, etc. In the present embodiment, a gap 205 may be fashioned in mask 200 to accommodate a user's nose. Paper tape strips 210 extend laterally from either side of mask 200. Some embodiments may comprise longer strips of paper tape that are oriented horizontally and/or vertically. In the present embodiment, mask 200 is affixed gauze side down to a thin plastic backing 215. Plastic backing 215 may provide single use dispensing of mask 200. Plastic backing 215 may be affixed to the gauze side of mask 200 without leaving a sticky surface on the gauze after mask 200 is separated from plastic backing 215 or may be affixed to paper tape strips 210 only. After being separated from plastic backing 215, paper tape strips 210 are still sticky, typically allowing for adhesion to a user's skin. In some embodiments, these paper tape strips may comprise a small tab of folded back tape that is non-sticky on both sides to generally enable a user to easily grip the tape strips.

In typical use of the present embodiment a user separates mask 200 and paper tape strips 210 from plastic backing 215. Holding paper tape strips 210, the user then places mask 200 over his or her eyes to generally provide light blocking Once mask 200 is in a satisfactory position, paper tape strips 210 are secured to the user's face. Mask 200 may be used alone or in conjunction with baseline strips and/or supplementary strips.

It is contemplated that some embodiments may comprise multiple microscopic holes in the light opaque tape layer to allow for small amounts of light to pass through the mask. These embodiments may be beneficial for users who are interested in eliminating artificial light during the night, yet would like to be awoken by sunlight in the morning. Furthermore, some embodiments may using materials or design that are not intended for sensitive skin users or may be irritating to the skin or eyelashes of users with normal skin. For example, without limitation, some of these embodiments may use plastic tape instead of paper tape, may use synthetic fiber instead of gauze, may involve putting tape into direct contact with the eyes, may involve putting electrical tape into direct contact with the skin, etc.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Having fully described at least one embodiment of the present invention, other equivalent or alternative methods of implementing a single use sleep mask according to the present invention will be apparent to those skilled in the art. Various aspects of the invention have been described above by way of illustration, and the specific embodiments disclosed are not intended to limit the invention to the particular forms disclosed. The particular implementation of the single use sleep mask may vary depending upon the particular context or application. By way of example, and not limitation, the single use sleep masks described in the foregoing were principally directed to sleeping aid implementations; however, similar techniques may instead be applied to eye protection, which implementations of the present invention are contemplated as within the scope of the present invention. For example, without limitation, some embodiments may be used in salons to generally prevent chemicals such as, but not limited to, dye or bleach from splashing into the eyes or in dentist offices to generally prevent water, saliva or foreign particles from entering the eyes during dental procedures. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. An apparatus comprising:
   a gauze layer comprising a gauze material, said gauze layer further comprising a first area, a gauze layer first side and a gauze layer second side, said gauze layer first side being configured to at least contact and cover a user's eyelid area where said gauze material mitigates irritation of the user's skin;
   a paper layer comprising a paper material, said paper layer further comprising a second area, a paper layer first side and a paper layer second side, said paper layer first side comprising an adhesive, a portion of said second area being configured to extend beyond said first area for removably joining to the user's skin; and
   a tape layer comprising an opaque flexible material, said tape layer further comprising a third area, a tape layer first side and a tape layer second side, said tape layer first side comprising an adhesive, said first area of said gauze layer having an area substantially the same size as said third area of said tape layer, said gauze layer, said paper layer and said tape layer being combined to form a sleep mask with said portion of said second area being configured to extend beyond said first area for removably joining to the user's skin, with said gauze layer being operable for covering and contacting the user's eyelid area, and with said tape layer being operable for mitigating passage of light to the user's eye.

2. The apparatus as recited in claim 1, in which said opaque flexible material comprises an electrical tape.

3. The apparatus as recited in claim 1, further comprising a plastic backing being joinable to said portion of said second area and removable from said portion prior to use of the sleep mask.

4. The apparatus as recited in claim 3, in which said plastic backing further comprises a fourth area being larger than said second area.

5. The apparatus as recited in claim 1, further comprising at least one tactile marker for indicating placement of the sleep mask during application to the user.

6. The apparatus as recited in claim 5, in which said tactile marker is formed on said tape layer.

7. The apparatus as recited in claim 1, in which said tape layer further comprises microscopic holes for enabling a filtered amount of light to pass.

8. The apparatus as recited in claim 1, in which a portion of said portion of said second area is non-adhesive to provide a gripping area during application and removal of the sleep mask.

9. The apparatus as recited in claim 1, further comprising supplementary strips for joining to the sleep mask and the user's skin for further mitigating passage of light.

10. The apparatus as recited in claim 1, in which said gauze layer, paper layer and said tape area are combined by joining said gauze layer second side to said paper layer first side and joining said tape layer first side to said paper layer second side.

11. The apparatus as recited in claim 10, in which the sleep mask is further configured to cover a single eyelid area.

12. The apparatus as recited in claim 1, in which said gauze layer, paper layer and said tape area are combined by joining said gauze layer second side to said tape layer first side and joining a portion of said paper layer first side to said tape layer second side.

13. The apparatus as recited in claim 12, in which the sleep mask is further configured to cover both eyelid areas.

14. The apparatus as recited in claim 1, in which the sleep mask is further configured as a single use apparatus.

15. An apparatus comprising:
   contacting means for covering a user's eyelid area where irritation of the user's skin is mitigated;
   means for removably joining said covering means to the user's skin;
   means for mitigating and reducing the passage of light through said covering means; and
   said contacting and covering means, removably joining means and said mitigating means being combined to form a sleep mask with said removably joining means being joinable to the user's skin, with said contacting and covering means covering and contacting the user's eyelid area, and with said mitigating means mitigating passage of light to the user's eye.

16. The apparatus as recited in claim 15, further comprising means for covering the back of the sleep mask and said covering means being removable from said back prior to use of the sleep mask.

17. The apparatus as recited in claim 15, further comprising tactile marker means for indicating placement of the sleep mask during application to the user.

18. An apparatus comprising:
   a gauze layer comprising a gauze material, said gauze layer further comprising a first area, a gauze layer first side and a gauze layer second side, said gauze layer first side being configured to at least contact and cover a user's single eyelid area where said gauze material mitigates irritation of the user's skin;
   a paper layer comprising a paper material, said paper layer further comprising a second area being larger than said first area, a paper layer first side and a paper layer second side, said paper layer first side comprising an adhesive, said paper layer first side being joined to said gauze layer second side where said paper layer first side creates an adhesive margin around said gauze layer for removably joining to the user's skin, said paper area further comprising a non-adhesive tab to provide a gripping area during application and removal from the user;
   a tape layer comprising an opaque flexible electrical tape, said tape layer further comprising a third area, a tape layer first side and a tape layer second side, said tape layer first side comprising an adhesive, said first area of said gauze layer having an area substantially the same size as said third area of said tape layer, said tape layer first side being joined to said paper layer second side with said tape layer at least covering said gauze layer to form a sleep mask with said adhesive margin being joinable to the user's skin, with said gauze layer being operable for covering and contacting the user's eyelid area, and with said tape layer being operable for mitigating passage of light to the user's eye;
   a tactile marker being formed on said tape layer for indicating placement of the sleep mask during application to the user; and
   a plastic backing comprising a fourth area being larger than said second area, said plastic backing being joinable to said adhesive margin and removable from said adhesive margin prior to use of the sleep mask.

19. The apparatus as recited in claim 18, further comprising supplementary strips for joining to the sleep mask and the user's skin for further mitigating passage of light.

20. The apparatus as recited in claim 18, in which said tape layer further comprises microscopic holes for enabling a filtered amount of light to pass.

* * * * *